US011713487B2

(12) United States Patent
Sarwal et al.

(10) Patent No.: US 11,713,487 B2
(45) Date of Patent: Aug. 1, 2023

(54) METHODS OF PREDICTING TRANSPLANT REJECTION RISK

(71) Applicant: The Regents of the University of California, Oakland, CA (US)

(72) Inventors: Minnie Sarwal, Portola Valley, CA (US); Marina Sirota, Belmont, CA (US); Silvia San Juan Pineda, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 356 days.

(21) Appl. No.: 16/631,145

(22) PCT Filed: Jul. 16, 2018

(86) PCT No.: PCT/US2018/042253
§ 371 (c)(1),
(2) Date: Jan. 14, 2020

(87) PCT Pub. No.: WO2019/014667
PCT Pub. Date: Jan. 17, 2019

(65) Prior Publication Data
US 2020/0224271 A1 Jul. 16, 2020

Related U.S. Application Data

(60) Provisional application No. 62/532,424, filed on Jul. 14, 2017.

(51) Int. Cl.
*C12Q 1/6883* (2018.01)
*G16H 50/30* (2018.01)
*G16B 20/20* (2019.01)
*G16H 10/40* (2018.01)
*G16B 30/00* (2019.01)

(52) U.S. Cl.
CPC ............ *C12Q 1/6883* (2013.01); *G16B 20/20* (2019.02); *G16B 30/00* (2019.02); *G16H 10/40* (2018.01); *G16H 50/30* (2018.01); *C12Q 2600/156* (2013.01)

(58) Field of Classification Search
CPC ........ G16H 50/30; G16H 10/40; G16B 30/00; G16B 20/20; C12Q 2600/156
See application file for complete search history.

(56) References Cited

U.S. PATENT DOCUMENTS

| 2010/0022627 | A1 | 1/2010 | Scherer |
| 2010/0190166 | A1* | 7/2010 | Halloran ............ C12Q 1/6883 435/6.1 |
| 2011/0262348 | A1 | 10/2011 | Movahedi et al. |
| 2012/0283123 | A1 | 11/2012 | Sarwal et al. |
| 2015/0337374 | A1 | 11/2015 | Perreault et al. |
| 2016/0060701 | A1 | 3/2016 | Schwartz et al. |
| 2016/0328515 | A1 | 11/2016 | Campagne |
| 2017/0011441 | A1 | 1/2017 | Buezas et al. |
| 2017/0114411 | A1 | 4/2017 | Mitchell et al. |
| 2018/0292384 | A1 | 10/2018 | Suthanthiran et al. |
| 2018/0346982 | A1 | 12/2018 | Schutz et al. |

FOREIGN PATENT DOCUMENTS

| CN | 107106679 | A | 8/2017 | |
| JP | 2013509883 | A | 3/2013 | |
| JP | 2014506893 | A | 3/2014 | |
| JP | 2015522590 | A | 8/2015 | |
| JP | 2016500323 | A | 1/2016 | |
| JP | 2016053039 | A | 4/2016 | |
| KR | 20150100716 | A | 9/2015 | |
| WO | WO-9426265 | A1 * | 11/1994 | ............. A61K 31/34 |
| WO | WO2008128333 | A1 | 10/2008 | |
| WO | 2011047090 | A1 | 4/2011 | |
| WO | WO-2014079946 | A1 * | 5/2014 | ............. A61P 37/06 |
| WO | 2015069933 | A1 | 5/2015 | |
| WO | WO-2015109097 | A1 * | 7/2015 | ........... C12Q 1/6883 |
| WO | 2016023019 | A2 | 2/2016 | |

OTHER PUBLICATIONS

Joris et al., 2012. A proposed algorithm predictive for cytotoxic T Cell Alloreactivity, J Immun 188: 1868-1873 Abstract, Fig. 1; p. 2, left hand column 1st-2nd paragraph.
Halloran et al., 2013. Antibody mediated rejection, and the injury repair response: new insights from the Genome Canada studies of kidney transplant biopsies, Kidney International 85: 258-264; whole document.
Sigdel et al, in Non-HLA antibodies to immunogenic epitopes predict the evolution of chronic renal allograft injury, J Am Soc Nephrol (2012) 23:750-63.
Jackson et al., Endothelial cell antibodies associated with novel targets and increased rejection. J Am Soc Nephrol (2015) 26:1161-71.
Taniguchi, et al., "Higher risk of kidney graft failure in the presence of anti-angiotensin II Type-1 receptor antibodies," American Journal of Transplantation, vol. 13, No. 10, pp. 2577-2589, 2013.

(Continued)

*Primary Examiner* — Joseph G. Dauner
(74) *Attorney, Agent, or Firm* — Kilpatrick Townsend & Stockton LLP

(57) ABSTRACT

In the field of transplant rejection, identified are SNPs wherein mismatches in variants present in a recipient and donor for such SNPs are predictive of transplant outcome, wherein the SNPs represent non-HLA loci newly implicated in rejection. By the invention, transplant outcomes such as elevated risk of antibody mediated rejection, elevated risk of T-cell mediated rejection, or low risk of rejection can be predicted by analyzing mismatches between donor and recipient for the enumerated SNPs. Certain SNPs enumerated are predictive of kidney transplant outcome. The compatibility of prospective donors can be assessed for a recipient, allowing for optimized donor-recipient pairing.

12 Claims, 3 Drawing Sheets

(56) References Cited

OTHER PUBLICATIONS

Goldfarb-Rumyantzev and Naiman in Genetic predictors of acute renal transplant rejection, Nephrol Dial Transplant (2010) 25:1039-47.
Ghisdal et al., Genome-wide association study of acute renal graft rejection, Am J Transplant (2016) 17(1):201-9.
Mesnard et al., in Exome sequencing and prediction of long-term kidney allogiafl function, PLoS Comput Biol (2016) PLOS Computational Biology doi: 10.1371/journal.pcbi.1005088.
Nicholls et al., Genome-Wide Analysis in Swine Associates Corneal Graft Rejection with Donor-Recipient Mismatches in Three Novel Histocompatibility Regions and One Locus Homologous to the Mouse H-3 Locus, PLOSoneDOI:10.1371/journal.pone.0152155, published Mar. 24, 2016.
Rittig et al., "Lehtin-binding sites in the anterior segment of the human eye," Graefe's Archive for Clinical and Experimental Ophthalmology, 1990, pp. 528-532, vol. 228, Germany.
Tuori et al., "Lectin binding in the antirior segment of the bovine eye," The Histochemical Journal, 1994, pp. 787-798, vol. 26, No. 10, Finland.
Banas et al., "Identification of a Urine Metabolite Constellation Characteristic for Kidney Allograft Rejection," Metabolomics, vol. 14, No. 9, Aug. 30, 2018, pp. 1-11.
Bloom et al., "Cell-Free DNA and Active Rejection in Kidney Allografts," Journal of the American Society of Nephrology, vol. 28, 2017, pp. 2221-2232.
Bonneau et al., "Metabolomics: Perspectives on Potential Biomarkers in Organ Transplantation and Immunosuppressant Toxicity," Clinical Biochemistry, vol. 49, Nos. 4-5, Jan. 12, 2016, 8 pages.
Application No. EP19900183.5, Extended European Search Report, dated Jul. 26, 2022, 6 pages.
Application No. EP20741257.8, Extended European Search Report, dated Oct. 24, 2022, 12 pages.
Ji et al., "Neutralization of Ocular Surface TNF-α Reduces Ocular Surface and Lacrimal Gland Inflammation Induced by In Vivo Dry Eye," Investigative Ophthalmology & Visual Science, vol. 54, Nov. 2013, pp. 7557-7566.
Nicholls et al., "Genome-Wide Analysis in Swine Associates Corneal Graft Rejection with Donor-Recipient Mismatches in Three Novel Histocompatibility Regions and One Locus Homologous to the Mouse H-3 Locus," PLoS One, vol. 11, No. 3, Mar. 24, 2016, pp. 1-12.
Nicholls et al., "Lectins in Ocular Drug Delivery: An Investigation of Lectin Binding Sites on the Corneal and Conjunctival Surfaces," International Journal of Pharmaceutics, vol. 138, No. 2, Jul. 26, 1996, pp. 175-183.
Application No. PCT/US2018/042253, International Search Report and Written Opinion, dated Dec. 24, 2018, 8 pages.
Recalde et al., "Transforming Growth Factor-β Inhibition Decreases Diode Laser-Induced Choroidal Neovascularization Development in Rats: P17 and P144 Peptides," Investigative Ophthalmology & Visual Science, vol. 52, Sep. 2011, pp. 7090-7097.
Salvadori et al., "Biomarkers in Renal Transplantation: An Updated Review," World Journal of Transplantation, vol. 7, No. 3, Jun. 24, 2017, pp. 161-178.
Sigdel et al., "A "Multi-omic" Analysis of Proteome and Metabolome for Acute Rejection and PVAN in Kidney Transplantation," American Transplant Congress, Jun. 4, 2018.
Sigdel et al., "Targeted Urine Metabolomics for Monitoring Renal Allograft Injury and Immunosuppression in Pediatric Patients," Journal of Clinical Medicine, vol. 9, No. 8, Jul. 22, 2020, pp. 1-14.
Wishart et al., "Metabolomics: The Principles and Potential Applications to Transplantation: Metabolomics in Organ Transplantation," American Journal of Transplantation, vol. 5, No. 12, Oct. 12, 2005, pp. 2814-2820.
Zheng et al., "GC/MS-based Urine Metabolomics Analysis of Renal Allograft Recipients with Acute Rejection," Journal of Translational Medicine, vol. 16, No. 1, Jul. 20, 2018, pp. 1-9.
Suciu-Foca et al., "Soluble Ig-Like Transcript 3 Inhibits Tumor Allograft Rejection in Humanized SCID Mice and T Cell Responses in Cancer Patients," The Journal of Immunology, vol. 178, No. 11, Jun. 1, 2007, pp. 7432-7441.

* cited by examiner

METHODS OF PREDICTING TRANSPLANT REJECTION RISK

CROSS-REFERENCE TO RELATED APPLICATIONS

This application claims priority to International Application No. PCT/US2018/042253, entitled "Novel Methods of Predicting Transplant Rejection Risk," filed on Jul. 16, 2018, which claims priority to U.S. Provisional Application No. 62/532,424, entitled "Novel Methods of Predicting Transplant Rejection Risk," filed on Jul. 14, 2017, each of which is incorporated by reference herein in its entirety.

STATEMENT REGARDING FEDERALLY SPONSORED RESEARCH OR DEVELOPMENT

Not applicable

BACKGROUND OF THE INVENTION

Transplant rejection is a serious problem affecting a large number of patients each year. For example, in the United States alone, about 2,500 transplanted kidneys are rejected and lost each month. Transplant occurs across histocompatibility antigen (HLA) barriers and requires life-long immunosuppression to effectively suppress injurious donor-specific immune responses, while conserving immune recognition of foreign and infectious antigens. Graft failure is a common transplant outcome. T-cell-mediated rejection (CMR) involves T-cell activation. Antibody-mediated rejection (AMR) involves B cell and plasma cell activation resulting in the generation of donor-specific antibodies (DSA), which bind to HLA and/or non-HLA (nHLA) molecules on the endothelium. The presence of pre-formed and de novo (newly formed) DSA, specific to donor-recipient mismatches is major risk factors for AMR, which results in both acute and chronic transplant injury and is the primary cause of accelerated early and late allograft loss.

The current approach for donor-recipient matching in organ transplant relies on evaluation of three major criteria—blood group compatibility, donor-recipient matching at the major HLA loci, and evaluation of sensitization risk by evaluation of pre-formed antibodies to major HLA loci.

HLA mismatch represents an important risk factor for graft rejection after transplant, as cells displaying non-host HLA types may be seen as foreign by the body's immune system, resulting in the rejection of the tissue/organ bearing those cells. However, graft injury and acute rejection can occur even in very well HLA-matched and even HLA-identical transplants, for example, kidney transplants. Recently, mismatched non-HLA antigens between the donor and recipient have been recognized to drive immunogenicity and transplant rejection.

For example, as disclosed in Sigdel et al, in Non-HLA antibodies to immunogenic epitopes predict the evolution of chronic renal allograft injury, *J Am Soc Nephrol* (2012) 23:750-63, pre-formed antibodies to various non-HLA antigens, including MIG (also called CXCL9), ITAC (also called CXCL11), IFN-γ, and glial-derived neurotrophic factor, are predictive of transplant injury in kidney. In another study of non-HLA antigens in kidney transplant, Jackson et al., Endothelial cell antibodies associated with novel targets and increased rejection. *J Am Soc Nephrol* (2015) 26:1161-71, show that antibodies to four antigenic targets expressed on endothelial cells, including endoglin, Fms-like tyrosine kinase-3 ligand, EGF-like repeats and discoidin I-like domains 3, and intercellular adhesion molecule 4, are implicated in transplant rejection. It is also known that anti-angiotensin II Type-1 receptor antibodies are associated with transplant rejection, for example, as disclosed in Taniguchi, et al., "Higher risk of kidney graft failure in the presence of anti-angiotensin II Type-1 receptor antibodies," American Journal of Transplantation, vol. 13, no. 10, pp. 2577-2589, 2013. These recent reports demonstrate that non-HLA antigens may play an important role in transplant rejection. Unfortunately, the specific non-HLA immunogenic antigenic donor-recipient mismatches that drive transplant rejection are difficult to predict and are currently poorly defined.

Genetic association studies of candidate non-HLA genes that are linked to transplant rejection have reported some single-nucleotide polymorphisms (SNPs) in genes encoding cytokines, chemokines, toll-like receptors, and VEGF as playing a role in transplant rejection, for example, as summarized by Goldfarb-Rumyantzev and Naiman in Genetic predictors of acute renal transplant rejection, *Nephrol Dial Transplant* (2010) 25:1039-47. A genome-wide association study by Ghisdal et al., Genome-wide association study of acute renal graft rejection, *Am J Transplant* (2016) 17(1):201-9, identified the loci PTPRO and CCDC67 being associated with a specific phenotype of CMR. In addition, as described by Mesnard et al., in Exome sequencing and prediction of long-term kidney allograft function, *PLoS Comput Biol* (2016), exome sequencing was used to assess the overall level of mismatch between donor and recipient pairs in cell surface proteins and this score was found be predictive of long-term graft function in kidney transplant recipients.

These reported results suggest that polymorphisms at the genetic level may be useful as predictors of transplant outcome. However, the scope of the previous work is limited and, to the knowledge of the inventors of the present disclosure, there have been no published studies that systematically identify non-HLA genetic factors that are predictive of rejection. Accordingly, there remains an ongoing need in the art for tools to comprehensively assess non-HLA mismatches between donor and recipient genes that predict or drive rejection in kidney and other types of transplants. There is a need in the art to identify non-HLA factors that contribute to immune response, transplant injury, and rejection. Furthermore, there is a need in the art for predictive tools that determine transplant rejection risk in prospective donor-recipient pairs, so that optimal pairing can be performed. Further, there is a need in the art for monitoring tools that assess the risk, onset, and severity of rejection in transplant recipients, allowing for intervention to prevent or reduce transplant injury.

SUMMARY OF THE INVENTION

Described herein are novel methods for the comprehensive identification of non HLA genetic factors that are predictive of transplant outcome. In a first aspect, the scope of the invention encompasses a novel strategy of identifying important non-HLA mismatches at the genetic level. This method reveals the specific polymorphisms that are predictive of poor transplant outcome, and may be applied to assess transplant risk for many types of transplants, in various populations.

In a second aspect, the scope of the invention encompasses novel methods of predicting transplant outcome using newly identified genetic mismatches that are predictive of rejection risk. These newly discovered genetic mismatches and predictive models based thereon provide a comprehensive tool for assessing rejection risk for prospective donor-recipient pairs so that donor-recipient pairing may be optimized.

In a third aspect, the scope of the invention encompasses novel methods for the assessment of recipient immune sensitization against a prospective or transplanted graft, by use of mismatched antigens disclosed herein. This method can be used prior to transplant to optimize donor-recipient pairing, or after transplant to monitor recipient immune response to the graft.

In a fifth aspect, the scope of the invention encompasses novel methods of treatment, wherein, guided by use of the diagnostic methods disclosed herein, optimized treatment may be administered to subjects in need of a transplant or having received a transplant.

In a sixth aspect, the scope of the invention encompasses novel diagnostic products and kits that may be utilized to perform the various diagnostic methods described herein.

DETAILED DESCRIPTION OF THE INVENTION

Figure 1:
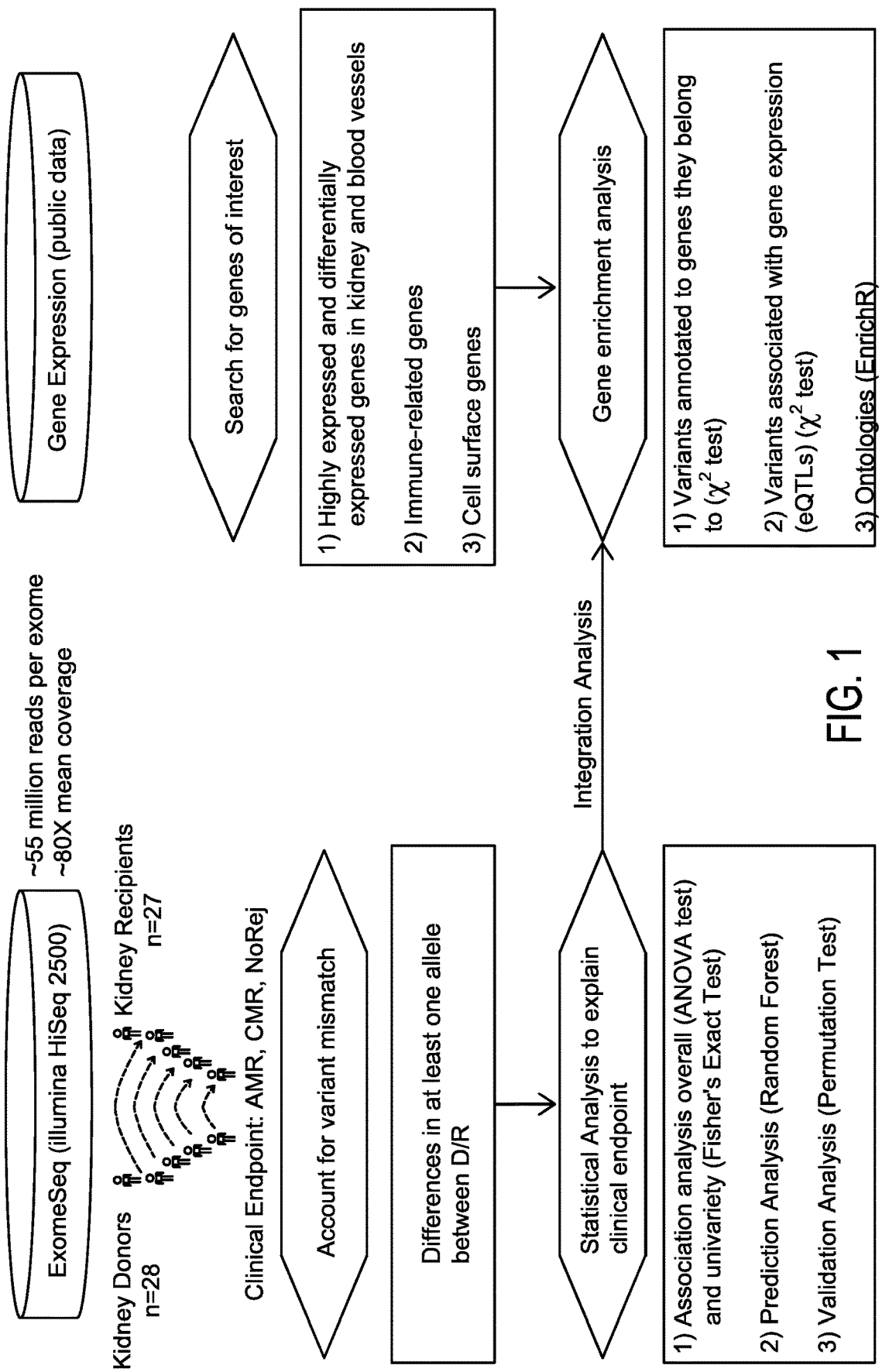
FIG. 1 depicts an overview of an exemplary implementation of the method of identifying genetic polymorphisms that are predictive of transplant outcome.

The various inventions disclosed herein encompass novel methods, processes, research tools, diagnostic tools, and other useful embodiments which enable the assessment of transplant rejection risk in a recipient.

The various inventions disclosed herein are directed to predicting transplant outcome for a graft. The graft may comprise any selected graft type, for example, a type selected from the group consisting of an organ, tissue, cells, kidney, heart, lung, liver, skin, cornea, intestine, pancreas, limb, digit, bone, ligament, cartilage, and tendon. References to a graft, as used herein will encompass whole organs and portions thereof.

Transplant is understood to occur between a donor individual and a recipient individual. In one embodiment, the recipient is a prospective recipient, i.e., a potential recipient wherein transplant of a graft from a prospective donor has not yet occurred. In one embodiment, the recipient is a realized donor wherein an allograft derived from a donor has been actually transplanted in the recipient.

The transplant donor and recipients may be humans, for example, the recipient may be a human patient in need of treatment. In alternative embodiments, the subjects may comprise non-human animals, for example veterinary patients or test animals. For convenience, the description provided herein will be directed to human subjects. It is understood that one of skill in the art may apply the methods and compositions described herein to non-human animals by utilizing homologs and/or orthologs of the genes and proteins disclosed herein.

The several embodiments of the invention are directed to predicting transplant outcome in donor-recipient pairs. Transplant outcomes may be defined as needed based on graft health and function and/or rejection processes and events. In some implementations, the transplant outcome is "no rejection," which may be defined as graft survival, preservation of graft function, and/or the absence of immune responses against the graft. In one implementation, the graft outcome is "rejection," which may be defined as injury to the graft, failure of the graft, immune response targeting the graft, or the manifestation of any process underlying rejection or symptom of rejection. In one implementation, the graft outcome is antibody-mediated rejection (AMR), which may be defined as the occurrence of any antibody-mediated injury to the graft, antibody-mediated graft failure, the presence of donor-specific antibodies (DSA) which bind to species present in the graft, for example on the endothelium of the transplant, and/or any other measure of antibody-mediated injury and/or rejection. In another implementation, the rejection is a cell-mediated rejection (CMR), which may be defined as injury to or failure of the graft mediated by T-cells activated against the transplanted tissue, the presence of activated T-cells against graft antigens, and/or any other measure of cell-mediated rejection.

Various methods disclosed herein are directed to the assessment of factors in a sample. The selected sample type may comprise any biological material. Exemplary samples include blood, serum, tissue, including graft tissue, interstitial fluid, skin, oral swabs or any other biological material comprising genetic information reflective of the graft and host genetic profiles. In one embodiment, donor samples are derived from the donor. In one embodiment, donor samples is derived from the graft after transplant in the recipient, for example, by biopsy.

Rejection-Associated Mismatches. In a first aspect, the objective of the invention is to systemically identify non-HLA genetic mismatches that are predictive of and/or which drive rejection, for various types of graft. Determination of such factors provides a means of better matching recipients with prospective donors, and for improved care following transplant as well. The strategy disclosed herein may be used to elucidate those genetic mismatches that are important in rejection.

In one implementation, the scope of the invention encompasses a method of identifying genetic mismatches that are predictive for transplant outcome. For a given gene, one (for a homozygous locus) or two (for a heterozygous locus) variants of the gene will be present in an individual. If the variant(s) present in the donor are not the same variants present in the recipient, this is considered a mismatch. These genetic mismatches, by various means, will manifest as differences between the proteins expressed by the graft tissue and those expressed by the recipient, i.e., the wherein the graft expresses a variant of a protein that is different from the variants expressed by the recipient. Non-host protein variants expressed by the graft are at risk of recognition by the immune system as foreign and thus graft tissue may become a target of various immune processes, causing significant graft injury and rejection.

Each rejection-associated genetic mismatch will occur at a specified polymorphic genetic locus, wherein two or more variants of the sequence at that locus are present in the population to which the donor and recipient belong. The variants may differ from one another by any structural or polymorphic difference. In one embodiment, the polymorphism is a SNP. The SNP may comprise a nonsynonymous substitution, comprising a change in a coding gene sequence that alters the amino acid sequence of the protein encoded thereby. The SNP may be directly causal for an incompatible protein phenotype (i.e. the structure of the protein is changed by the genetic polymorphism), or the SNP may be regulatory, causing expression of a protein in a way that renders it antigenic to the recipient. In another embodiment, the SNP is a marker for an incompatible protein phenotype (i.e. the polymorphism is linked to factors that result in an incompatible graft protein). In other embodiments, the polymorphism is allelic, chromosomal, is based on variable numbers of tandem repeats, or comprises an insertion or deletion mutation.

In some cases, the polymorphism is in the coding sequence of a protein. In other cases, the polymorphism is in a regulatory sequence, for example comprising an expression quantitative trait locus (eQTL). An eQTL controls the expression of one or more genes, for example with respect to timing, location, magnitude of expression, etc. An eQTL polymorphism between the donor and recipient may result in differential expression of one or more proteins.

For most such polymorphisms, a mismatch between donor and recipient variants of the gene is associated with an increased risk of rejection. For a small subset of polymorphisms, a mismatch is associated with a lower risk of rejection. As used herein, rejection-associated polymorphism will refer to any polymorphism, e.g. at the genetic or protein level which is predictive of transplant outcome.

In a first aspect, the scope of the invention encompasses methods of identifying rejection-associated genetic mismatches in a selected population. The selected population will encompass a plurality of individuals having any number of shared demographic characteristics, for example, subjects of a selected nation or group of nations having similar health parameters, or subjects of a selected race or ethnic group.

The method of identifying rejection associated genetic mismatches encompasses the performance of a post-hoc analysis of mismatch data in subjects having known transplant outcomes. An exemplary strategy for identifying rejection associated polymorphisms is depicted in FIG. 1.

In one embodiment, invention encompasses a method of identifying rejection-associated genetic mismatches that are predictive of transplant outcome for a selected graft type, comprising the steps of:
  selecting a plurality of donor-recipient pairs wherein each recipient has received a graft comprising the selected graft type from a donor;
  monitoring transplant outcome for each recipient for a selected period of time following receipt of the graft;
  obtaining a sample from each of the donor and the recipient of each donor-recipient pair;
  performing a selected genetic analysis on the samples to create a genetic profile for each donor and recipient;
  creating a mismatch profile for each donor-recipient pair comprising a set of mismatched polymorphic gene loci variants between the donor and recipient; and
  performing a post-hoc statistical analysis to identify polymorphic gene loci for which a mismatch is predictive of transplant outcome.

By the analysis, rejection-associated genetic mismatches having a contribution to transplant risk may be identified. Each such mismatch encompasses a genetic locus (site of the mismatch) and two or more variants that are expressed at the locus, wherein mismatched donor and recipient variants have an effect on transplant outcome.

It will be understood that the method of the invention is not limited to order of the steps presented above and that the scope of the invention encompasses variations in the order of the steps. For example, the samples may be obtained prior to transplant or after transplant.

The selected period of time following the transplant procedure during which transplant outcome is monitored may be any period of time, for example, at least 3 months, at least 6 months, at least 9 months, at least one year, at least 18 months, or at least two years following the transplant procedure.

The transplant outcome may comprise one of two or more outcomes defined by measures of transplant success or failure, for example, based on graft survival, graft function, or graft injury. In one embodiment, for example, the outcomes comprise: no rejection, wherein the graft did not fail and/or did not experience significant injury or impairment of function during the selected time period following transplant; AMR, wherein one or more antibody-mediated processes implicated in graft injury and/or failure is implicated during the selected time period following transplant; and CMR, wherein wherein one or more T Cell-mediated processes is implicated in graft injury and/or failure during the selected time period following transplant. In another embodiment, the outcomes are no rejection, defined as above, and rejection, defined as any graft injury and/or failure during the selected time period following transplant For the method to be successful, the plurality of donor-recipient pairs will comprise a plurality of recipients having each of the selected transplant outcomes during the selected time period following transplant, such that statistically valid samples of each outcome are included in the analysis. Such numbers will depend on the variability of the donor and recipient genomes and transplant outcomes, and the desired degree of statistical rigor. Sample sizes for each outcome may comprise, for example, at least five recipients; at least ten recipients, at least 20 recipients; at least 50 recipients; and at least 100 recipients.

The genetic analysis may be any genetic analysis for determining genetic differences between the donor and recipient. In one embodiment, the genetic analysis is a whole genome analysis comprising a sequencing of the entire genome or a selected portion thereof. In one embodiment, the genetic analysis is an exosome analysis wherein all or a subset of protein-coding gene sequences are sequenced. In one embodiment, the analysis is a transcriptome analysis wherein all or a subset of expressed genes are sequenced. In a preferred implementation, a comprehensive analysis of all genes is performed to capture all polymorphisms of interest. In an alternative implementation, a subset of genes is selected for the analysis, for example, organ specific genes.

The analysis may be performed by the use of any appropriate DNA analysis tools known in the art, for example by hybridization-based techniques (e.g. dynamic allele-specific hybridization, SNP gene arrays), enzyme based methods (e.g. RFLP, PCR analyses, primer extensions assays, and oligonucleotide ligation assays), and other detection methods (e.g. single strand conformation polymorphisms, temperature gradient gel electrophoresis, denaturing HPLC). In another implementation, rejection-associated mismatches are assessed at the protein level, by comparing protein sequences obtained from suitable samples, using methods known in the art, for example by the use of immunoassays, protein chips, and other detection techniques.

The statistical analysis may comprise any statistical method known in the art for correlating mismatches with transplant outcome. For example, analysis methodologies that may be used include: logistic regression analysis, linear discriminant analysis, partial least squares-discriminate analysis, multiple linear regression analysis, multivariate non-linear regression, backwards stepwise regression, threshold-based methods, tree-based methods, Pearson's correlation coefficient, Support Vector Machine, generalized additive models, supervised and unsupervised learning models, cluster analysis, and other statistical model generating methods known in the art.

The statistical analysis may be further employed to generate a predictive model that relates mismatch data to predicted transplant outcome. The input of the predictive model will be a set of donor-recipient mismatches and the output of the model will be a score, classification, or probability, or other output bearing on the risk transplant rejection for the set of mismatches. The inputs may further include selected thresholds, including probability thresholds, sensitivity thresholds, specificity thresholds, or statistical significance thresholds, wherein the output will fall within the specified thresholds.

The predictive model may be based upon the number of mismatches, for example, wherein risk increases with the number of mismatches. The predictive model may be based upon the type of mismatches, for example, wherein AMR risk increases with the number of of AMR-associated mismatches or the risk of CMR increases with the number of CMR-associated mismatches. In another embodiment, the mismatches are assigned weighted values reflective of their relative contributions to rejection. The model may also account for other variables relevant to transplant risk, such as donor and recipient age, sex, race, number of previous transplants, and the degree of variant mismatches at HLA loci, presence of rejection-associated antibodies, creatinine, or other indicators of transplant risk.

The output of the model may comprise a probability score or other score indicating the statistical significance or likelihood of the predicted outcome being correct. In one embodiment, the output of the predictive model is an index score, being a value within a defined range that is reflective of transplant outcome. In one embodiment, the output of the model is a probability score, for example, a. Z-score or a probability of rejection occurring, for example, a probability of AMR or CMR occurring. In one embodiment, the output of the model is a classification, for example classification of the transplant as no rejection, AMR rejection, or CMR rejection. In another embodiment, the classifications are low risk of rejection, intermediate risk of rejection, or high risk of rejection.

By the method of the invention, the inventors have advantageously identified a number of rejection-associated genetic mismatches, listed in Table 1. These rejection-associated genetic mismatches are broadly applicable to many graft types, including kidney. As denoted in Table 1, certain rejection-associated genetic mismatches of the invention are "AMR" mismatches, comprising mismatches that are associated with antibody-mediated rejection. As denoted, certain rejection-associated genetic mismatches of Table 1 are "CMR" mismatched, comprising mismatches that are associated with cell-mediated rejection. A small handful of the rejection-associated genetic mismatches of Table 1 are beneficial mismatches, comprising a mismatch that is associated with better transplant outcome, e.g. non-rejection (denoted "NoRej" in Table 1). The mismatches specified for ATP2B2, PLEKHM3, SEC13, and TBCEL listed in Table 1 comprise beneficial mismatches. As denoted, certain of the polymorphisms in Table 1 comprise kidney rejection-associated genetic mismatches, comprising mismatches particularly relevant to (but not exclusively predictive for) rejection in kidney transplant.

Table 1. Table 1 lists SNPs associated with transplant rejection outcome. Each SNP is a SNP known in the art, identified by a registered identifier, for example as may be accessed in the National Center for Biotechnology Information dbSNP database or as otherwise known in the art. Each SNP listing comprises a gene identifier (gene), locus information (chromosome and location), two variant gene sequences (reference and substitution sequences), and classification (Rejection type) as CMR, AMR, or NoRej. Certain SNPs are indicated to be kidney associated SNPs.

TABLE 1

| Gene | SNP registered | Chromosome | Position | Ref Base | Substitution | Rejection Type | Kidney |
| --- | --- | --- | --- | --- | --- | --- | --- |
| ABCA3 | rs170447 | 16 | 2349371 | T | C | AMR | |
| ABCC6 | rs58394656 | 16 | 16291816 | G | C | AMR | YES |
| ABR | rs2586306 | 17 | 909451 | A | T | AMR | |
| AGR2 | rs4719480 | 7 | 16834551 | C | A | CMR | YES |
| AIM1L | rs12562454 | 1 | 26671084 | G | T | CMR | |
| AIM1L | rs57268417 | 1 | 26671248 | A | G | CMR | |
| AIM1L | rs11247924 | 1 | 26673076 | G | A | CMR | |
| AIM1L | rs11247925 | 1 | 26673108 | C | T | CMR | |
| AP3D1 | rs2072306 | 19 | 2109019 | T | C | AMR | YES |
| AP3D1 | rs20567 | 19 | 2110746 | G | A | AMR | YES |
| AP3D1 | rs2074959 | 19 | 2111649 | T | C | AMR | YES |
| AP3D1 | rs2066775 | 19 | 2115493 | A | G | AMR | YES |
| AP3D1 | rs4807203 | 19 | 2127272 | A | G | AMR | YES |
| ATM | . | 11 | 108196003 | C | T | CMR | |
| ATP2B2 | rs35674 | 3 | 10368577 | C | A | NoRej | |
| BCHE | rs2686409 | 3 | 165495400 | G | A | AMR | |
| C19orf54 | rs3745213 | 19 | 41248009 | C | T | CMR | |
| CARD19 | rs10821071 | 9 | 95874428 | G | A | AMR | |
| CDC123 | rs2271804 | 10 | 12252217 | G | A | AMR | |
| CDC123 | rs10951 | 10 | 12292344 | A | G | AMR | |
| CDYL2 | rs9940301 | 16 | 80641906 | G | A | AMR | |
| CDYL2 | rs9933302 | 16 | 80641931 | T | C | AMR | |
| CELSR2 | rs11102967 | 1 | 109817245 | C | T | AMR | |
| CHRNA10 | rs2231547 | 11 | 3687626 | T | G | CMR | |
| CHRNA10 | rs2231546 | 11 | 3687651 | C | T | CMR | |
| CNTN2 | rs2229868 | 1 | 205041158 | C | T | AMR | |
| COL16A1 | rs2297674 | 1 | 32163950 | G | C | AMR | |
| CRTAM | rs3134421 | 11 | 122742460 | A | T | AMR | |
| CSMD3 | rs55980973 | 8 | 113655644 | A | T | AMR | |

TABLE 1-continued

| Gene | SNP registered | Chromosome | Position | Ref Base | Substitution | Rejection Type | Kidney |
|---|---|---|---|---|---|---|---|
| CSMD3 | rs6992564 | 8 | 113662299 | T | G | AMR | |
| CSMD3 | rs7839990 | 8 | 113697567 | A | G | AMR | |
| CYP11A1 | rs12442401 | 15 | 74659535 | A | G | AMR | |
| DDX25, CDON | rs635346 | 11 | 125818405 | G | A | AMR | |
| EFCAB3 | rs11079476 | 17 | 60472623 | C | T | AMR | |
| FAH | rs2043691 | 15 | 80472431 | C | A | AMR | |
| FAM129B | rs2243558 | 9 | 130289615 | C | G | AMR | YES |
| FAM129B | rs2251409 | 9 | 130286150 | A | G | AMR | YES |
| FBXO15 | rs12962744 | 18 | 71749359 | G | A | AMR | YES |
| FRMD3 | rs871790 | 9 | 86037233 | C | T | AMR | |
| GABRR1 | rs1796743 | 6 | 89888744 | C | T | AMR | |
| GSG1L | rs117918036 | 16 | 27840271 | C | T | CMR | |
| HMCN2 | rs7858563 | 9 | 133260316 | T | G | AMR | |
| IL7 | rs13264965 | 8 | 79672953 | A | G | AMR | |
| IL7 | rs4739138 | 8 | 79673952 | T | C | AMR | |
| INPP5D, ATG16L1 | rs34547900 | 2 | 234117915 | C | A | AMR | |
| ISYNA1 | rs1045631 | 19 | 18545786 | G | T | AMR | |
| ITGAE | rs3809805 | 17 | 3704483 | G | A | AMR | |
| KDM4C | rs7029684 | 9 | 7174430 | T | C | AMR | |
| KIAA1755 | rs41282822 | 20 | 36869396 | G | A | CMR | |
| KIAA1755 | rs41282824 | 20 | 36869769 | C | T | CMR | |
| KIAA1755 | rs112586932 | 20 | 36874313 | G | T | CMR | |
| KRT74 | rs75004274 | 12 | 52960884 | C | T | CMR | |
| LAMA5 | rs8124907 | 20 | 60913127 | A | G | AMR | YES |
| LINC00226, LINC00221 | • | 14 | 106781032 | C | T | CMR | |
| LOC100128233, MIR4708 | rs1256522 | 14 | 65738029 | C | T | AMR | |
| LOC100128233, MIR4708 | rs1256523 | 14 | 65738126 | A | G | AMR | |
| LOC10028933 | rs8101688 | 19 | 12319301 | C | T | AMR | |
| LOC100506082, OR52B4 | rs61884560 | 11 | 4308726 | T | G | CMR | |
| LOC390705, ENPP7P13 | rs71255153 | 16 | 33539560 | A | C | CMR | |
| MUC3A | rs78118592 | 7 | 100550837 | C | T | AMR | |
| MUC3A | rs200242471 | 7 | 100550841 | C | A | AMR | |
| MYOM2 | rs3817699 | 8 | 2024437 | C | T | AMR | |
| MYOM2 | rs3817700 | 8 | 2024446 | C | T | AMR | |
| NLRP8 | rs306456 | 19 | 56499337 | C | T | AMR | |
| NUP98 | rs12293627 | 11 | 3704770 | C | T | CMR | |
| OLIG2 | rs56307226 | 21 | 34400237 | G | C | CMR | |
| OR51F1 | rs1030723 | 11 | 4790471 | G | A | AMR | |
| OR51F1 | rs11033793 | 11 | 4790474 | T | C | AMR | |
| OR51F1 | rs10836609 | 11 | 4791178 | C | A | AMR | |
| OR51F1 | rs10836610 | 11 | 4791181 | T | G | AMR | |
| OR5AC2 | rs6439602 | 3 | 97806999 | T | C | AMR | |
| OR8D1 | rs7107539 | 11 | 124180282 | A | C | AMR | |
| OR8G1 | rs4268525 | 11 | 124121199 | G | C | AMR | |
| OR8G1 | rs2466636 | 11 | 124134552 | C | T | AMR | |
| OR8G2 | rs2466613 | 11 | 124096247 | G | A | AMR | |
| OR8G5 | rs2512168 | 11 | 124135009 | G | A | AMR | |
| OR8G5 | rs2512167 | 11 | 124135438 | G | A | AMR | |
| OR8G5 | rs2466701 | 11 | 124135481 | C | T | AMR | |
| PLD2 | rs1052748 | 17 | 4720469 | C | T | AMR | |
| PLEKHM3 | rs720632 | 2 | 208693261 | C | G | NoRej | |
| PNPLA6 | rs577219 | 19 | 7615585 | T | G | AMR | |
| PNPLA6 | rs574663 | 19 | 7614677 | C | T | AMR | |
| POMT2 | rs3815625 | 14 | 77751729 | T | C | AMR | |
| POTEA | rs66932611 | 8 | 43147975 | T | G | AMR | |
| PRH1-PRR4 | rs11522329 | 12 | 11182989 | T | C | AMR | |
| PSEN2 | rs11405 | 1 | 227069677 | T | C | AMR | |
| PSEN2 | rs2236910 | 1 | 227073410 | G | C | AMR | |
| PSEN2 | rs2802267 | 1 | 227078955 | T | C | AMR | |
| PSEN2 | rs10753428 | 1 | 227081622 | A | G | AMR | |
| PTCHD3 | rs7071851 | 10 | 27703234 | A | G | AMR | |
| PUM3 | rs2292000 | 9 | 2831149 | A | C | AMR | |
| RASA3 | rs4074317 | 13 | 114747187 | G | C | AMR | |
| RASA3 | rs2274716 | 13 | 114781868 | G | A | AMR | |
| ROCK1P1 | rs8096198 | 18 | 120645 | C | T | AMR | |
| RPF2 | rs12191479 | 6 | 111318588 | A | G | CMR | |

TABLE 1-continued

| Gene | SNP registered | Chromosome | Position | Ref Base | Substitution | Rejection Type | Kidney |
|---|---|---|---|---|---|---|---|
| RTN4 | rs17046589 | 2 | 55237049 | T | G | CMR | YES |
| RTN4RL2 | rs2258835 | 11 | 57243588 | A | G | AMR | |
| SEC13 | rs35670 | 3 | 10353550 | T | C | NoRej | |
| SGCD | rs284445 | 5 | 156187928 | C | T | AMR | |
| SHC2 | rs112380345 | 19 | 439055 | G | A | AMR | |
| SIK3 | rs4938316 | 11 | 116764582 | C | T | AMR | |
| SLC13A1 | rs12706498 | 7 | 122788665 | G | A | AMR | YES |
| SLC17A5 | rs3734518 | 6 | 74304415 | G | C | AMR | |
| SLC4A11 | rs3803956 | 20 | 3214581 | C | T | AMR | YES |
| SLC6A17 | rs12737742 | 1 | 110709720 | G | A | AMR | |
| SLC7A7 | rs1061040 | 14 | 23242828 | T | C | AMR | YES |
| SLU7 | rs2961940 | 5 | 159831803 | A | G | AMR | |
| SNAI1 | rs4647954 | 20 | 48599549 | T | C | AMR | |
| SNAPC1 | rs1254677 | 14 | 62233806 | A | G | AMR | |
| SPATA41 | rs4965642 | 15 | 100889442 | A | G | AMR | |
| SPATA7 | rs4904448 | 14 | 88852166 | G | A | AMR | |
| STYXL1 | rs8565 | 7 | 75630274 | T | C | AMR | |
| TBCEL | rs10502246 | 11 | 120924200 | T | C | NoRej | |
| TLE4 | rs2297499 | 9 | 82267732 | C | G | AMR | |
| TMEM171 | rs7448965 | 5 | 72419041 | C | C | CMR | YES |
| TNIK | rs13074171 | 3 | 170843782 | A | A | CMR | |
| TUBGCP2 | rs1573040 | 10 | 135107370 | A | A | CMR | |
| WBSCR17 | rs4719110 | 7 | 70785929 | A | A | AMR | |
| WWOX | rs11545028 | 16 | 78133671 | T | T | AMR | |
| ZBTB40 | rs209727 | 1 | 22837849 | T | T | AMR | |
| ZNF280D | rs28620278 | 15 | 56959028 | T | T | AMR | |
| ZNF280D | rs12911191 | 15 | 56961272 | A | A | AMR | |
| ZNF836 | rs17696575 | 19 | 52660783 | G | G | CMR | |

Predicting Transplant Outcome. In one implementation, the scope of the invention encompasses a method of predicting transplant outcome for a selected donor-recipient pair. The general method comprises the steps of:
  obtaining a sample from the donor, and, by the sample, identifying the donor variants expressed at polymorphic loci of rejection-associated genetic mismatches;
  obtaining a sample from the recipient, and, by the sample, identifying, the recipient variants expressed at polymorphic loci of rejection-associated genetic mismatches;
  compiling a mismatch profile comprising the set of mismatched variants between the donor and recipient; and
  inputting the mismatch profile to a predictive model predictive model relating mismatches to transplant outcome, wherein the output of the predictive model is a prediction of transplant outcome for the donor-recipient pair.

In one implementation, the predictive method is applied to a prospective donor-recipient pair. In a prospective donor-recipient pair, no transplant has yet occurred. In a prospective donor-recipient pair the recipient comprises a subject in need of a transplant and the donor comprises a potential source of the needed graft. In this context, the methods of the invention are applied in order to assess the compatibility of the donor and recipient. The resulting measure of compatibility may then be used as a decision tool for determining if the putative transplant should go forward. For example, if the risk of rejection exceeds a selected threshold value, the putative transplant may be foregone in favor of a more compatible donor. In one implementation, the method is performed to screen a pool of multiple potential donors, in order to identify compatible and incompatible donors within the pool.

In an alternative implementation, the tools of the invention are applied post-transplant. In this context, the method may be applied to determine a subject's risk of rejection, for example, AMR or CMR rejection.

In the predictive methods of the invention, the variants analyzed may comprise the alternative sequences for one or more SNPs listed in Table 1, for example, one or more SNPs selected from the group consisting of rs1030723; rs1045631; rs1052748; rs1061040; rs10753428; rs10821071; rs10836609; rs10836610; rs10951; rs11033793; rs11079476; rs11102967; rs112380345; rs11405; rs11522329; rs11545028; rs12442401; rs1254677; rs1256522; rs1256523; rs12706498; rs12737742; rs12911191; rs12962744; rs13264965; rs170447; rs1796743; rs200242471; rs2043691; rs20567; rs2066775; rs2072306; rs2074959; rs209727; rs2229868; rs2236910; rs2243558; rs2251409; rs2258835; rs2271804; rs2274716; rs2292000; rs2297499; rs2297674; rs2466613; rs2466636; rs2466701; rs2512167; rs2512168; rs2586306; rs2686409; rs2802267; rs284445; rs28620278; rs2961940; rs306456; rs3134421; rs34547900; rs3734518; rs3803956; rs3809805; rs3815625; rs3817699; rs3817700; rs4074317; rs4268525; rs4647954; rs4719110; rs4739138; rs4807203; rs4904448; rs4938316; rs4965642; rs55980973; rs574663; rs577219; rs58394656; rs635346; rs6439602; rs66932611; rs6992564; rs7029684; rs7071851; rs7107539; rs78118592; rs7839990; rs7858563; rs8096198; rs8101688; rs8124907; rs8565; rs871790; rs9933302; rs9940301; rs11247924; rs11247925; rs112586932; rs117918036; rs12191479; rs12293627; rs12562454; rs13074171; rs1573040; rs17046589; rs17696575; rs2231546; rs2231547; rs3745213; rs41282822; rs41282824; rs4719480; rs56307226; rs57268417; rs61884560; rs71255153; rs7448965; rs75004274; rs35674; rs720632; rs35670; and rs10502246. In various implementations, mismatches for variants of at least five, at least ten, at least 20, at least 50, at least 100, or all or substantially all of the SNPs of Table 1 are analyzed.

In one implementation, the variants analyzed may comprise the alternative sequences for one or more SNPs, identified by random forest analysis, for example, at least five, at least ten, at least 20 or at least 50 SNPs selected from the group consisting of rs28620278; rs1052748; rs1061040;

rs10821071; rs10951; rs11079476; rs11247924; rs11247925; rs11405; rs11522329; rs11545028; rs1254677; rs12562454; rs1256522; rs1256523; rs12737742; rs12962744; rs1573040; rs2043691; rs20567; rs2066775; rs2072306; rs2074959; rs2236910; rs2243558; rs2251409; rs2274716; rs2297499; rs2297674; rs2686409; rs284445; rs28620278; rs34547900; rs35670; rs35674; rs3734518; rs3745213; rs3803956; rs3815625; rs3817699; rs3817700; rs4074317; rs4647954; rs4807203; rs4904448; rs4938316; rs57268417; rs574663; rs577219; rs58394656; rs61884560; rs635346; rs6439602; rs7071851; rs7107539; rs71255153; rs720632; rs8101688; rs8565; rs871790; rs9933302; and rs9940301.

In one embodiment, the transplant outcome includes AMR and the variants analyzed comprise the variants of one or more AMR SNPs selected from the group consisting of rs1030723; rs1045631; rs1052748; rs1061040; rs10753428; rs10821071; rs10836609; rs10836610; rs10951; rs11033793; rs11079476; rs11102967; rs112380345; rs11405; rs11522329; rs11545028; rs12442401; rs1254677; rs1256522; rs1256523; rs12706498; rs12737742; rs12911191; rs12962744; rs13264965; rs170447; rs1796743; rs200242471; rs2043691; rs20567; rs2066775; rs2072306; rs2074959; rs209727; rs2229868; rs2236910; rs2243558; rs2251409; rs2258835; rs2271804; rs2274716; rs2292000; rs2297499; rs2297674; rs2466613; rs2466636; rs2466701; rs2512167; rs2512168; rs2586306; rs2686409; rs2802267; rs284445; rs28620278; rs2961940; rs306456; rs3134421; rs34547900; rs3734518; rs3803956; rs3809805; rs3815625; rs3817699; rs3817700; rs4074317; rs4268525; rs4647954; rs4719110; rs4739138; rs4807203; rs4904448; rs4938316; rs4965642; rs55980973; rs574663; rs577219; rs58394656; rs635346; rs6439602; rs66932611; rs6992564; rs7029684; rs7071851; rs7107539; rs78118592; rs7839990; rs7858563; rs8096198; rs8101688; rs8124907; rs8565; rs871790; rs9933302; and rs9940301. In various implementations, mismatches for variants of at least five, at least ten, at least 20, at least 50, at least 75, or all or substantially all of the AMR SNPs of Table 1 are analyzed.

In one embodiment, one or more AMR SNPs used in the analysis are SNPs from genes wherein multiple mismatches predictive of AMR rejection are found. Such genes include AP3D1 (for example, SNPs rs2072306, rs20567, rs2074959, rs2066775, and rs4807203), CDC123 (for example, SNPs rs2271804 and rs10951), CDYL2 (for example, SNPs rs9940301 and rs9933302), CSMD3 (for example, SNPs rs55980973, rs6992564, and rs7839990), FAM129B (for example, SNPs rs2251409 and rs2251409), IL7 (for example, SNPs rs13264965 and rs4739138), MUC3A (for example SNPs rs78118592 and rs200242471), MYOM2 (for example, SNPs rs3817699 and rs3817700), OR51F1 (for example SNPs rs1030723, rs11033793, rs10836609, and rs1083661), OR8G1 (for example, SNPs rs4268525 and rs2466636), OR8G5 (for example, SNPs rs2512168, rs2512167, and rs2466701), PNPLA6 (for example, SNPs rs577219 and rs574663), PSEN2 (for example, SNPs rs11405, rs2236910, rs2802267, and rs10753428), RASA3 (for example, SNPs rs4074317 and rs2274716), ZNF280D (for example, SNPs rs28620278 and rs12911191), and genes from the SLC family (for example, SNPs rs1061040, rs3803956, rs12706498, rs12737742, and rs3734518).

In one embodiment, the transplant outcome includes CMR and the variants analyzed comprise the variants of one or more CMR SNPs selected from the group consisting of rs11247924; rs11247925; rs112586932; rs117918036; rs12191479; rs12293627; rs12562454; rs13074171; rs1573040; rs17046589; rs17696575; rs2231546; rs2231547; rs3745213; rs41282822; rs41282824; rs4719480; rs56307226; rs57268417; rs61884560; rs71255153; rs7448965; rs75004274. In various implementations, mismatches for variants of at least five, at least ten, at least 20, or all or substantially all of the CMR SNPs of Table 1 are analyzed.

In one embodiment, one or more CRM SNPs used in the analysis are SNPs from genes wherein multiple mismatches predictive of CMR rejection are found. Such genes include AIM1L (for example, SNPs rs12562454, rs57268417, rs11247924, and rs11247925), CHRNA10 (for example, SNPs rs2231547 and rs2231546), and KIAA1755 (for example, SNPs rs112586932, rs41282822, and rs41282824).

In one embodiment, the mismatch analysis utilizes one or more SNPs comprising non-synonymous exonic SNPs. Non-synonymous exonic AMR SNPs include rs1030723; rs1052748; rs11033793; rs12737742; rs2466613; rs2512167; rs2512168; rs28620278; rs4904448; rs7107539; and rs78118592. Non-synonymous CMR exonic SNPs include rs11247924; rs11247925; rs12562454; rs2231546; rs2231547; rs41282824; rs57268417; and rs75004274.

In one embodiment, the transplant type is kidney and the prediction of transplant outcome analyzes the variants of one or more kidney-associated SNPs selected from the group consisting of rs1061040; rs12706498; rs12962744; rs17046589; rs20567; rs2066775; rs2072306; rs2074959; rs2243558; rs2251409; rs3803956; rs4719480; rs4807203; rs58394656; rs7448965; and rs8124907.

Figure 2:
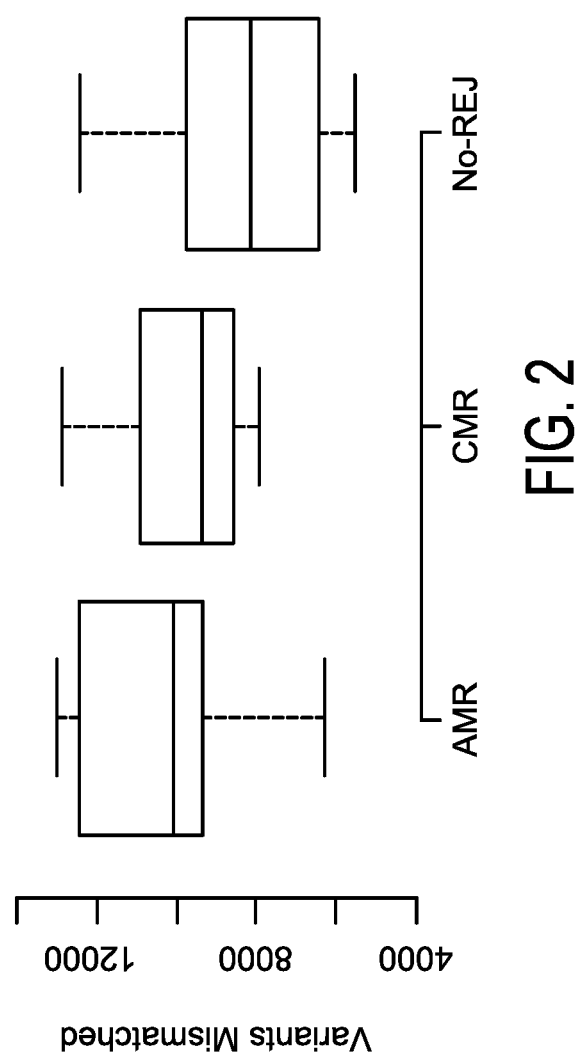
FIG. 2 is a boxplot representing the distribution of mismatched variants in each donor-recipient pair, stratified by the clinical endpoints of antibody-mediated rejection (AMR), T-cell-mediated rejection (CMR), and no-rejection (NoRej)

In one embodiment, the number of mismatched variants is utilized as a predictor of transplant outcome. In one embodiment, the transplant outcome includes AMR and no rejection, and an elevated risk of AMR rejection is indicated by a greater number of mismatched variants than observed in the no rejection outcome. For example, as depicted in FIG. 2, a significantly greater number of mismatched variants is predictive of AMR. In one embodiment, an intermediate number of mismatched variants is predictive of CMR.

In an exemplary embodiment, the scope of the invention comprises a method of predicting transplant outcome by an analysis of variant mismatches wherein the transplant outcome includes AMR, CMR, and no rejection and the variants analyzed comprise variants of SNPs comprising at least five, at least ten, at least 20, at least 50, at least 100 or all or substantially all of the SNPs of Table 1. In one embodiment, the at least five, at least ten, at least 20, or the at least 50 SNPs of Table 1 are selected from the group consisting of rs28620278; rs1052748; rs1061040; rs10821071; rs10951; rs11079476; rs11247924; rs11247925; rs11405; rs11522329; rs11545028; rs1254677; rs12562454; rs1256522; rs1256523; rs12737742; rs12962744; rs1573040; rs2043691; rs20567; rs2066775; rs2072306; rs2074959; rs2236910; rs2243558; rs2251409; rs2274716; rs2297499; rs2297674; rs2686409; rs284445; rs28620278; rs34547900; rs35670; rs35674; rs3734518; rs3745213; rs3803956; rs3815625; rs3817699; rs3817700; rs4074317; rs4647954; rs4807203; rs4904448; rs4938316; rs57268417; rs574663; rs577219; rs58394656; rs61884560; rs635346; rs6439602; rs7071851; rs7107539; rs71255153; rs720632; rs8101688; rs8565; rs871790; rs9933302; and rs9940301. In one embodiment, the transplant comprises a kidney transplant. In one embodiment, the donor is a prospective donor. In one embodiment, AMR is predicted by a greater number of mismatches than observed in CMR and no rejection.

Tangible Products. In certain embodiments, the scope of the invention encompasses tangiel products or kits comprising a collection of tangible products that may be used to detect variants implicated in mismatches predictive of transplant outcome. In implementing the predictive methods of the invention, various tangible components may be used to detect the selected variants present in the samples. In one implementation, the predictive method is achieved by use of an array, i.e. a substrate or plurality of substrates (e.g. beads) comprising immobilized probes complementary to nucleic acid sequences specific for the selected variants. In one embodiment, the array is a SNP array. In one embodiment, the array utilized in the practice of the predictive method will selectively detect variants of one or more of the SNPs listed in Table 1. In various implementations, the array of the invention comprises probes that can detect variants of SNPs comprising at least five, at least ten, at least 20, at least 50, at least 100, or all or substantially all of the SNPs of Table 1. In one embodiment, the array will detect variants of SNPs comprising at least five, at least ten, at least 50, or all or substantially all of the SNPs of the group consisting of rs28620278; rs1052748; rs1061040; rs10821071; rs10951; rs11079476; rs11247924; rs11247925; rs11405; rs11522329; rs11545028; rs1254677; rs12562454; rs1256522; rs1256523; rs12737742; rs12962744; rs1573040; rs2043691; rs20567; rs2066775; rs2072306; rs2074959; rs2236910; rs2243558; rs2251409; rs2274716; rs2297499; rs2297674; rs2686409; rs284445; rs28620278; rs34547900; rs35670; rs35674; rs3734518; rs3745213; rs3803956; rs3815625; rs3817699; rs3817700; rs4074317; rs4647954; rs4807203; rs4904448; rs4938316; rs57268417; rs574663; rs577219; rs58394656; rs61884560; rs635346; rs6439602; rs7071851; rs7107539; rs71255153; rs720632; rs8101688; rs8565; rs871790; rs9933302; and rs9940301.

In other implementations, the predictive methods of the invention are achieved by use of primer sets or other collections of tangible products for the selective amplification and/or detection of nucleic acids specific to the selected variants. In one embodiment, the primer set or collection of tangible products for the selective amplification and/or detection of variants comprises a plurality of primers that amplify the variants of SNPs comprising at least five, at least ten, at least 20, at least 50, at least 100, or all or substantially all of the SNPs of Table 1. In one embodiment, the SNPs comprise at least five, at least 10, at least 50, or all or substantially all of the SNPs selected from the group consisting of rs28620278; rs1052748; rs1061040; rs10821071; rs10951; rs11079476; rs11247924; rs11247925; rs11405; rs11522329; rs11545028; rs1254677; rs12562454; rs1256522; rs1256523; rs12737742; rs12962744; rs1573040; rs2043691; rs20567; rs2066775; rs2072306; rs2074959; rs2236910; rs2243558; rs2251409; rs2274716; rs2297499; rs2297674; rs2686409; rs284445; rs28620278; rs34547900; rs35670; rs35674; rs3734518; rs3745213; rs3803956; rs3815625; rs3817699; rs3817700; rs4074317; rs4647954; rs4807203; rs4904448; rs4938316; rs57268417; rs574663; rs577219; rs58394656; rs61884560; rs635346; rs6439602; rs7071851; rs7107539; rs71255153; rs720632; rs8101688; rs8565; rs871790; rs9933302; and rs9940301.

Sensitization Assay. The newly discovered rejection-associated genetic mismatches disclosed herein provide the art with tools for assessing a recipient's compatibility with the graft of a donor. The various polymorphic gene variants disclosed herein code for proteins, wherein graft proteins comprising variants not present in the host (i.e. derived from a mismatched variant) are potentially antigenic and their presence in a transplanted graft may lead to immune-mediated graft injury. Such proteins may be used in diagnostic methods to assess potential or ongoing recipient immune activity against mismatched protein. As used herein, "variant coded antigens" will refer to proteins coded by each variant of a polymorphic rejection-associated gene loci. Variant coded antigens will encompass whole proteins as well as fragments or truncations thereof, to the extent that the fragments or truncations encompass polymorphic structural regions arising from the polymorphism in the rejection-associated gene. As used herein, "mismatched variant antigen" will refer to a variant coded antigen which is present in the donor and not in the recipient.

In one implementation, the scope of the invention comprises a method of assessing a recipient's immune sensitization to mismatched variant antigens. The method comprises the following steps:

obtaining a sample from the donor, and, by the sample, identifying the donor variants expressed at polymorphic loci of rejection-associated genetic mismatches;

obtaining a sample from the recipient, and, by the sample, identifying, the recipient variants expressed at polymorphic loci of rejection-associated genetic mismatches;

compiling a mismatch profile comprising the set of genetic variants present in the donor and not present in the recipient; and assaying a sample derived from the recipient to detect immune elements directed against mismatched variant antigens, wherein the presence of immune elements directed against such variant antigens is indicative of immune-mediated transplant risk.

By this method, the recipient's sensitization to mismatched variant antigens likely present in the graft may be assessed. By random chance or genetic predisposition, a recipient may have one or more pre-formed donor-specific immune elements targeting antigens found in the graft and not in the recipient, creating rejection risk is the graft is performed or has been performed. The immune elements may comprise effectors of AMR or effectors of CMR, for example, antibodies and T cells, which selectively bind mismatched antigens of the graft. The degree of rejection risk will generally increase with the number of distinct mismatched antigen variants targeted by the immune system of the recipient and/or the diversity and abundance of immune elements targeting such antigens.

In a first implementation, the sensitization assay is performed in a prospective donor pair. By this method, the compatibility of a prospective donor-recipient pair may be evaluated based on the immune status of the recipient prior to transplant. This aids in the selection of compatible donors and exclusion of incompatible donors.

In a second implementation, the sensitization assay is performed in a realized donor pair. By this method, the sensitization of the recipient's immune system against mismatched graft antigens may be assessed, providing a measure of ongoing rejection risk or ongoing immune-mediated graft injury. The assessment may be performed over time to monitor the recipient's immune response against mismatched graft antigens.

In performing the methods, the variant coded antigens may comprise proteins coded by the variants of one or more SNPs of Table 1, for example, variants coded by SNPs of Table 1 comprising at least five, at least ten, at least 20, at least 50, at least 100, or all or substantially all of the SNPs of Table 1. In one embodiment, the risk of AMR rejection is assessed by recipient sensitivity to variant coded antigens coded by one or more AMR SNPs of Table 1, for example, at least ten, at least 20, at least 50, or at least 75 AMR SNPs of Table 1. In one embodiment, the risk of CMR rejection is assessed by recipient sensitivity to variant coded antigens coded by one or more CMR SNPs of Table 1, for example, at least five, at least 20, or at least 50 CMR SNPs of Table 1. In one embodiment, the risk of kidney transplant rejection is assessed by recipient sensitivity to variant coded antigens coded by one or more kidney-associated SNPs listed in Table 1. In one embodiment, the variant coded antigens are proteins coded by the variants of non-synonymous exonic SNPs, including non-synonymous exonic AMR SNPs: rs1030723; rs1052748; rs11033793; rs12737742; rs2466613; rs2512167; rs2512168; rs28620278; rs4904448; rs7107539; and rs78118592; and non-synonymous CMR exonic SNPs: rs11247924; rs11247925; rs12562454; rs2231546; rs2231547; rs41282824; rs57268417; and rs75004274.

The detection of antibodies directed to mismatched variant antigens may be performed using any appropriate tools in the art for the detection of antibodies directed to a specific antigen. Exemplary methods include the use of immunoprecipitation assays, antigen arrays, antibody ELISA and other antibody detection methods known in the art. In one embodiment, the scope of the invention encompasses the tangible components of a kit or assay wherein such kit or assay is directed to the detection of antibodies directed to one or more variant coded antigens coded for by the polymorphic genetic rejection-associated genes of Table 1, for example, being directed to the detection of at least 5, at least ten, at least 20, at least 50, or at least 100 such variant coded antigens.

The detection of CMR effectors, such as CD8$^+$ T cells, can be performed using methods known in the art for the detection of antigen-specific immune cells, for example by secreted cytokine assays, flow cytometry assays, Enzyme-Linked ImmunoSpot assays, and others techniques known in the art. In one embodiment, the scope of the invention encompasses the tangible components of a kit or assay wherein such kit or assay is directed to the detection of CD8$^+$ T cells or other CMR effectors directed to one or more variant coded antigens coded for by the polymorphic genetic rejection-associated genes of Table 1, for example, being directed to the detection of at least 5, at least ten, at least 20, at least 50, or at least 100 such variant coded antigens.

Methods of Treatment. In another aspect, the scope of the invention encompasses methods of treating a subject. In a first implementation, the method encompasses a method of treating a subject in need of a graft by the following process:
  assessing the risk of transplant rejection between the subject and one or more putative donors by the use of selected rejection-associated genetic mismatches between the recipient and the one or more putative donors;
  selecting a compatible donor based on the assessed risk of transplant rejection;
  performing a transplant of a graft from the selected donor to the recipient.

In another implementation, the method of the invention comprises a method of ameliorating the risk of transplant rejection in a recipient that has received a graft from a donor, comprising the steps of:
  performing an assessment of transplant rejection risk for the donor-recipient pair by the use of of rejection-associated genetic mismatches between the recipient and the donor;
  administering a treatment to ameliorate the risk of transplant rejection based upon the assessment.

For example, in one embodiment, the assessment is an elevated risk of rejection. In one embodiment, the assessment is a low risk of rejection. In one embodiment, the assessment is an elevated risk of AMR. In one embodiment, the assessment is an elevated risk of CMR. Based upon the assessment, appropriate treatment may be applied to the subject.

For example, if the risk of rejection is determined to be high, the subject may be subjected to more frequent monitoring of graft function or graft injury. Likewise, if the risk of rejection is determined to be elevated, more aggressive treatment to mitigate the rejection risk may be applied to the subject post-transplant than would be applied to a subject having low rejection risk. Conversely, if the risk of transplant rejection is low, immunosuppressive treatment and monitoring may be reduced. In one embodiment, if the risk of CMR is found to be elevated, treatments appropriate for mitigating CMR are administered, such as the use of corticosteroids and T cell-depleting agents. In one embodiment, if the risk of AMR is elevated, treatments appropriate for treating AMR are applied, for example, plasmapheresis, administration of intravenous immune globulin, and B cell depletion.

EXAMPLES

Non-Histocompatibility Antigen Mismatched Variants Improve the Ability to Predict Antibody-Mediated Rejection Risk in Kidney Transplant. Study Design. Fifty-five individuals paired by donor-recipient (D/R) from 27 kidney transplant (tx) from 28 kidney donors (one recipient had to go through a second tx) were selected and sequenced using blood DNA. Each blood sample was obtained from the donor and the recipient prior to tx. Recipients were selected in one of three clinical categories based on the presence or absence of biopsy-proven rejection in the first 6 months after tx. There were 14 recipients confirmed with AMR, seven recipients confirmed with CMR, and seven stable recipients without rejection. Patients with normal 6-month protocol biopsies and stable graft function based on the evaluation of the serum creatinine were grouped in the NoRej group. Patients with biopsy-confirmed acute rejection, based on an indication biopsy for graft dysfunction (>20% rise in the serum creatinine above baseline) were classified into either CMR or AMR based on standardized Banff classification of kidney allograft histopathology. To enrich for patients with post-transplant biopsy-confirmed rejection in the first 6 months, patients were selected who were highly sensitized (mean cPRA 47±45). Twelve of the 14 recipients in the AMR cohort tested positive for DSA at the time of transplant and 13 of 14 tested positive for DSA at time of biopsy. Patients received thymoglobulin for induction and were maintained on steroids, tacrolimus, and mycophenolate mofetil for their maintenance immunosuppression regimen. To enrich for patients with post-transplant biopsy-confirmed rejection in the first 6 months patients were selected who were highly sensitized (mean cPRA 47±45). Molecular HLA typing was performed by reverse sequence specific oligonucleotide hybridization. Donor-specific HLA antibodies were evaluated using solid-phase immunoassays performed. Unacceptable HLA antigen assignments and CPRA calculations were based on HLA antibody specificities strong enough to yield a positive flow cytometric crossmatch. In this cohort, exomeSeq and clinical data were integrated with functionally relevant gene expression data leveraging selected publically available datasets. The overall design is showed in FIG. 1.

DNA Extraction and exomeSeq. DNA was extracted from PBMCs collected from donor and recipients and standard exome capture methods were applied. The exome captured libraries were then sequenced on the on the 55 DNA blood samples with an average of 55 million reads per exome and mean coverage of 80×. Raw data were aligned to the human genome build 37 (hg19) using bwa-mem (0.7.15). Fastqc (0.11.5) was used as a quality control tool for the sequence data. Picard (1.141) was used for marking duplicates in the bam file. The Genome Analysis Toolkit (GATK) (3.4-46) software package for analysis of high-throughput sequencing data was used to perform the subsequence analysis. GATK's BaseRecalibrator was used to generate recalibrated and realigned bam files. GATK's HaplotypeCaller was used for the variant calling and the filtering was done using variant quality score recalibration according to GATK Best Practices recommendations. The variant recalibrator evaluates variants in a two-step process, each performed by a distinct tool: (1) VariantRecalibrator: create a Gaussian mixture model by looking at the annotations values over a high-quality subset of the input call set and then evaluate all input variants. This step produces a recalibration file. (2) ApplyRecalibration: apply the model parameters to each variant in input VCF files producing a recalibrated VCF file in which each variant is annotated with its VQSLOD value. In addition, this step will filter the calls based on this new VQSLOD score by adding lines to the FILTER column for variants that do not meet the specified VSQLOD threshold. Multiallelic SNPs and insertions and deletions (indels) were excluded. The variants using were annotated ANNOVAR identifying a total number of 515,899 variants restricted to the autosomal chromosomes. From these variants, only the variants that were called in at least 95% of the samples were considered, resulting in a total of 488,539 variants for subsequent analyses.

D/R Variant Mismatch. Variant mismatch between D/R pairs was measured considering one allele difference in at least one of the individuals. The data matrix for the analysis accounted for the mismatch considering all the variants and D/R pairs. With the total number of mismatches, an ANOVA-test was performed to account for the global association with the clinical endpoints (AMR, CMR, or NoRej) adjusting the model by a "genomic distance," which takes into account the race and relatedness information of each D/R pair. The genomic distance was obtained by assessing the first two principal components in a principal component analysis (PCA) with the 1000 Genomes Project panel and obtaining the Euclidean distance by pairs.

Association Analysis Considering Clinical Endpoints. The association of the variants was assessed with the clinical endpoints. Using a data matrix with the 28 D/R pairs as columns and all the variants with at least one pair mismatched (472,400 variants) as rows, Fisher's exact test was applied to find an association between each specific mismatched variant and the clinical endpoints. To find the mismatched variants that are associated with an increased risk of AMR and/or CMR, the number of variants of which the number of pairs was higher in each group in comparison to the others was observed.

Gene Enrichment Analysis. Publicly available datasets were used to functionally annotate observed variants and genes of interest. Using standard tools, four lists of genes of interest were generated: (1 and 2) Genes highly expressed and differentially expressed (DE) in kidney and blood vessels, (3) genes that are immune related, and (4) genes that are expressed on the cell surface. To perform the gene enrichment analysis, the variants associated with AMR were annotated to genes in two different ways: (1) considering the genes they are located in and (2) considering the eGenes from the expression quantitative trait loci (eQTL) analysis from GTEx in blood vessels and whole blood. Considering these two annotations for the variants, an enrichment analysis using a chi square-test with the four lists of genes (kidney, blood vessels, immune related, and cell surface). The annotated variants were analyzed with the EnrichR tool.

Prediction Analysis of Clinical Endpoints. Random forest (RF) was applied to overpass the MT correction problem and a lack of statistical power. RF is a machine learning technique for prediction and classification problems that works well with small sample size and uses the generation of several random trees to avoid the detection of false positives and over-fitting. RF does not perform a variable selection by itself, so the R package variable selection method was applied that proposes a variable selection method based on RF by minimizing the out of bag error (OOB) rate. In order to find a specific subset of variants that classify the samples based on the clinical endpoints. In RF, there is no need for cross-validation or a separate test set to get unbiased estimates since each tree is built using a bootstrapped sample from the original data. One-third of the cases are left out from the construction of the tree and it is used as a test set to obtain the OOB error.

Results. The different clinical endpoints distributed 28 recipients in one of three categories: (1) NoRej group (n=7): stable graft function (stable serum creatinine) and protocol biopsy-confirmed absence of any significant pathology or rejection; (2) CMR group (n=7): graft dysfunction (>20% increase in serum creatinine from baseline) and biopsy-confirmed CMR using Banff criteria; and (3) AMR group (n=14): graft dysfunction and biopsy-confirmed antibody-mediated rejection using Banff criteria, with or without DSA to major HLA antigens. To perform analysis of D/R variant mismatching, exomeSeq was performed on the 28 D/R pairs prior to kidney organ tx. All patients were on similar maintenance immunosuppression with mycophenolate mofetil, tacrolimus, and steroids, and induction with thymoglobulin. Demographic parameters, inclusive of cause of ESRD, were matched among the three subsets of patients.

The total number of D/R variant mismatches assessed prior to tx was noted to be significantly higher in the AMR group (ANOVA-test, AMR vs. NoRej, p-value=0.02). Additional analysis of specific D/R variant mismatches that specifically associate with one or more clinical endpoints, identified a novel set of 123 variants (Fisher's exact test, p-value <0.001). A minimal set of 65 variants (from the set of 123 variants) was selected with RF (accuracy error=0.03) and provided clean classification of all three-sample phenotype outcomes for the recipients after tx, with very robust performance on repeated permutation testing. Genes that were highly enriched in the transplanted organ (kidney), to the anatomical site most affected by AMR (blood vessels), to select for candidates enriched in the rejection process (immune related), and to select candidates that are more likely to be recognized by the recipients' immune response (cell-surface expression).

Higher Number of Pre-tx D/R Mismatched Variants Associate with Increased Risk of Post-tx AMR. The variant differences per D/R pair were evaluated with respect to the human reference genome build 37 (hg19). Variant mismatches were considered if one of the alleles between the donor and the recipient at a particular SNP position was different. 472,400 variants were identified that were mismatched in at least one D/R pair: 386,958 had at least one mismatch in the AMR group, 268,722 in the CMR group, and 248,531 in the NoRej group. A significantly increased number of mismatched variants in the AMR group in comparison with the NoRej group was observed (ANOVA p-value=0.04) (FIG. 2), and as expected, it was observed that the number of mismatched variants was also dependent on race differences between the donor and the recipient and whether the D/R pair was related. As the AMR group was noted to have the largest number of D/R race mismatches, the AMR and race mismatches on the number of variant mismatches was analyzed in each D/R pair by performing PCA. As expected, the donors and recipients from the study clustered further or closer according to the number of mismatched variants, and also clustered together with the population that was consistent with their self-reported race. Genomic distance was accounted for considering the Euclidean distance in the plot by D/R pair. This variable was used to adjust the previous ANOVA analysis and it was observed that AMR was still significantly associated with a significantly higher number of mismatches (p-value=0.02; AMR vs. NoRej).

Figure 3:
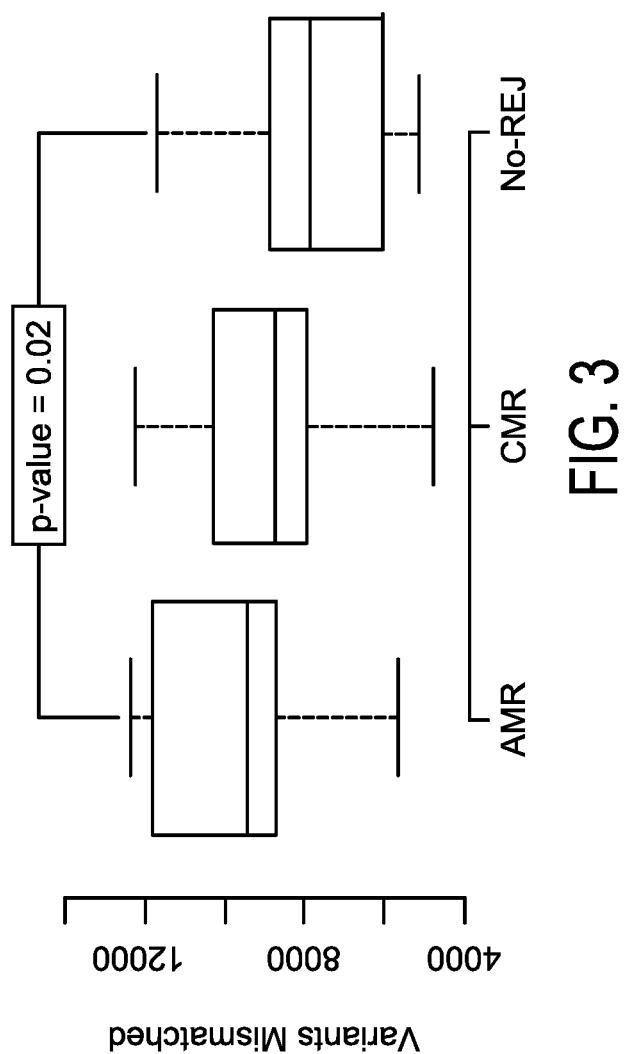
FIG. 3 is a boxplot representing the distribution of mismatched variants in each group per clinical endpoint restricted only to non-synonymous exonic variants, for antibody-mediated rejection (AMR), T-cell-mediated rejection (CMR), and no-rejection (NoRej).

To evaluate the biological significance of the observed mismatched variants, their functional classification was examined. 25% of the mismatched variants were exonic with almost half of them being non-synonymous and thus more likely to have an impact on protein function. An ANOVA-test considering only the non-synonymous variants was applied and similar to the previous results, these were found to be significantly higher for the D/R pair where the recipient went on to develop AMR after tx (FIG. 3).

D/R Mismatched Variants Are Associated with AMR after Transplantation. 123 unique variants (19 non-synonymous) (p<0.001; Fisher's exact test) were identified as nominally associated with either of three clinical endpoints of AMR, CMR, or NoRej after tx, with an incidence of 87% in the AMR, 57% in the CMR, and 20% in the NoRej. To best assess the most significant variants for each clinical group, the maximal impact of variant sets was evaluated for each D/R pair cohort, in comparison to the other two; again, it was noted (as seen earlier by global analysis) an enrichment of mismatched variants for AMR, with 94 variants most enriched for AMR (AMR>CMR>NoREJ), 25 variants for CMR (CMR>NoRej>AMR), and 4 variants enriched for low immune risk and NoRej (NoRej>AMR>CMR). To account for the independence of race mismatch and relatedness between the D/R pairs, it was tested if the 123 variants were associated with any of these two variables using Fisher's exact test and none were significant corroborating the independence.

D/R Mismatched Variants in the HLA Region Have Less Impact on Post-tx AMR than Mismatched nHLA Variants. None of the 123 variants identified belonged to the HLA region. To address the potential role of HLA mismatches in these samples, an association analysis was performed between the HLA mismatches considering nine major HLA genes (HLA-A, HLA-B, HLA-C, HLA-DRB1, HLA-DRB3, HLA-DRB4, HLA-DRB5, HLA-DQB1, HLA-DPB1) with clinical endpoints and presence of DSA. HLA measures by serotype and exomeSeq showed highly concordant results. This analysis was performed considering the data measured by the antigens detected by HLA serotyping (standard of care) and accounting the number of variants mismatches in these nine HLA genes. Significant results were not observed for the association of HLA with the clinical endpoints of rejection or no rejection after tx (p-value=0.3, HLA antigen data; p-value=0.6 HLA exomeSeq data), though in both cases, there is a trend for a higher number of HLA mismatches in the rejection group. As expected, a higher number of DSA had borderline significance with a higher number of HLA mismatches (p-value=0.07, HLA antigen data). In addition, as a positive control for the data analysis, an association analysis was conducted between HLA mismatches, race mismatch and relatedness, and as expected, significantly decreased number of HLA mismatches was found in related D/R pairs (p-value=0.03) and a non-significant increase number of HLA mismatches in race mismatched D/R pairs.

The Variants Associated with Increase Risk of Post-tx AMR Are Enriched in Relevant Gene Sets. To assess the biological impact of the 123 significantly associated mismatched variants the impact of the variants was evaluated on different gene expression datasets. A first assumption was that a mutation in the corresponding gene would result in a mutated mRNA and consequently a mutated protein in the donor or recipient kidney, which can trigger an antibody response in the recipient resulting in renal allograft rejection and injury. A second assumption is that a mutation in the gene would result in different mRNA expression (eQTL) in the same gene (cis) or at another locus (trans), which would then produce a change in the expression of a protein in the donor kidney, consequently trigger an antibody response in the recipient, and drive renal allograft rejection and injury. With this in mind, the variants were annotated to genes using the eQTL analysis from GTEx. Only the relevant eQTLs in whole blood and blood vessels were considered, since the key pathobiology of AMR injury in the donor kidney occurs in the donor microvasculature. The 94 variants associated with AMR were found to reside in 72 unique genes, as some genes had more than one variant, a factor that may be used to weight their biological relevance in predictive models. Genes with multiple variants were AP3D1 (5 variants—1 synonymous), CDC123 (2 variants), CDYL2 (2 variants), CSMD3 (3 variants), FAM129B (2 variants), IL7 (2 variants), MUC3A (2 variants—1 non-synonymous, 1 synonymous), MYOM2 (2 variants), OR51F1 (4 variants—2 non-synonymous), OR8G1 (2 variants), OR8G5 (2 non-synonymous variants, 1 synonymous), PNPLA6 (2 variants), PSEN2 (4 variants—1 synonymous), RASA3 (2 variants), ZNF280D (2 variants—1 non-synonymous), and the SLC family (5 variants—1 non-synonymous, 2 synonymous). Seven out of the 19 non-synonymous variants (37%) were located in AMR specific genes. The 25 variants associated with CMR resided in 22 unique genes, the following of which had multiple variants: AIM1L (4 non-synonymous variants), CHRNA10 (2 non-synonymous variants) and KIAA1755 (3 variants—1 non-synonymous, 1 synonymous). For CMR, 7 out of 19 (37%) non-synonymous variants were located in genes with multiple variants.

When mapping for eQTLs was performed, 37 eQTLs were found to be enriched in the dataset pertaining to blood vessels and 22 were enriched in the dataset pertaining to whole blood, with several identified "hotspots," defined by variants that were associated with more than one gene or genes that were associated with more than one variant. It was observed that the eQTLs were only found with variants associated with risk of post-tx AMR.

Thirdly, the enrichment of significant SNPs was evaluated within four sets of genes, functionally relevant to the study. Using publically available data, genes that are highly expressed or DE in kidney (the transplanted organ of interest), the endothelium (the target cell of interest in AMR), in immune cells (the effector cells of interest in rejection), and cell surface expressed genes (that may have a higher probability of interaction between the mutated donor antigenic epitope and the recipient antibody paratope). For each set of genes, an enrichment analysis was performed using the $\chi^2$-test. When considering the variants previously identified to be associated with risk of post-tx AMR, it was found that statistically significant enrichment in the immune-related genes (p-value=0.007) and cell-surface genes (p-value=4.7*10$^{-7}$). For CMR, significant enrichment for the immune-related genes was also found (p-value=0.02).

In addition, variant eQTL analysis in AMR identified significant enrichment for kidney-specific genes (eQTL blood vessels: p-value=0.004; eQTL whole blood: p-value=0.0005) and blood vessels (eQTL blood vessels: p-value=0.02; eQTL whole blood: p-value=0.002).

A gene set enrichment analysis was performed to find common biological pathways and processes in rejection specific genes that harbor mismatched variants, using the web-based tool EnrichR (42, 43). Importantly, the 72 unique genes associated with AMR were enriched for active trans-membrane transporter activity (GO:0022804) (p-value=0.0008) and immune response-activating cell-surface receptor signaling pathway (GO:0002429) (nominal p-value=0.1) When the 22 genes that are associated exclusively with CMR were assessed, it was found enrichment in CD4+ T-cells and CD8+ T-cells (nominal p-value=0.1).

Machine Learning Techniques Provide a Robust Prediction of Post-tx Rejection Risk Based on Novel D/R Mismatched Variants. In the previous analysis using Fisher's exact test, a single variant was analyzed at a time in a large number of statistical tests, which in combination with the small sample size, resulted in no variants passing the multiple hypothesis correction threshold. Also, modeling a multi-class problem (more than two categories for the clinical endpoints) further adversely influences statistical power. To address this problem, a more advanced statistical method was used to circumvent the issue of statistical power with a machine learning technique, RF. RF builds a classification model for the response variable (clinical endpoints) using all predictors (mismatched variants) quantifying the importance of each predictor. To find whether there is a group of mismatched variants that can predict the study clinical endpoints the a Variable Selection Using Random Forests software package (VSURF) was used. After applying the VSURF algorithm, 65 mismatched variants were found with a very small OOB error rate (0.03), where OOB measures the accuracy of the final forest. In a binary heatmap, the three clinical endpoints perfectly cluster together, independent of race mismatch and relatedness. These variants were also tested with a Fisher's exact test to find association with race mismatch and relatedness as aforementioned and no significant association was observed. To further verify that results are not due to random chance, a permutation test was performed shuffling the labels of the clinical endpoints from the original data set.

Discussion. Antibody-mediated rejection is a major cause of allograft dysfunction and graft loss as a result of the development of de novo DSA to donor-specific HLA antigen mismatches with the recipient after tx. The principal targets of the AMR response are the highly polymorphic HLA antigens, but the rejection process has also been observed in HLA-identical siblings, suggesting a critical role for D/R nHLA antigen mismatches that may also drive pathogenic antibodies to these mismatched nHLA antigens in AMR. The results described herein show a significant increase in the number of mismatched variants prior to tx, which significantly correlate with the development of biopsy-confirmed acute rejection in the recipient after tx.

The total number of variants that mismatch by D/R pairs is higher when the recipient goes on to develop AMR after tx. In addition, a highly refined set of variants was identified that can accurately predict immune risk stratification of patients before tx, into those that develop different clinical endpoints after tx of either biopsy-confirmed AMR, biopsy-confirmed CMR or stable function and no rejection. None of these newly identified variants were located in the HLA region, even though the patients involved in this study were sensitized to various HLA antigens. Importantly, the AMR group was in race mismatch while NoRej was enriched in relatedness, demonstrating that the findings are independent for both, race mismatch and relatedness.

Further analysis of the 94 variants significantly associated with an increased risk of post-tx AMR located in 72 unique genes enriched in immune-related function, supporting their role in the rejection process; in addition, these variants also map to genes that are more likely to be expressed on the cell-surface, suggesting that changes in the expression/function of these genes are more likely to be recognized by the recipients' immune system, and support the possible generation of antibody responses to nHLA targets.

It was also observed that specific nHLA variant mismatches impact the development of CMR, as the remaining 25 variants associated exclusively with post-tx CMR. These 25 variants map to 22 unique genes and are highly enriched in immune-related function involving CD4+ T-cells and CD8+ T-cells. This study also highlights the existence of key intrinsic differences between the triggers and mechanisms of injury in AMR and CMR.

The genes associated with rejection in this study are biologically relevant; specifically those that also have multiple associated variants (AP3D1, CDC123, CDYL2, CSMD3, FAM129B, MUC3A, MYOM2, OR51F1, OR8G1, OR8G5, PNPLA6, PSEN2, RASA3, ZNF280D, AIM1L, CHRNA10 and KIAA1755 and SLC-family). 15 out of 18 of these genes associate with risk of post-transplant AMR, and the majority (74%) of non-synonymous variants are located in these genes and in three other genes that associate with the risk of post-tx CMR (AIM1L, CHRNA10, and KIAA1755). These variants are likely to be biologically significant for their impact on post-tx rejection.

In addition, biological relevance in the context of AMR can be ascribed to many of the identified variants as eQTLs (DNA sequence variants that can influence the expression level of one or more genes) that are significantly enriched in blood vessels and kidney, the target organs of injury in AMR. Many hotspots in the endothelial eQTLs were observed where more than one variant is related to one gene and vice versa. For example, the two SNPs (rs2251409 and rs2243558) located in the FAM129B gene are associated with three different genes (SLC2A8, ZNF79, and RPL12) enriched in the vascular tissues. On the other hand, other genes are associated with multiple variants, e.g., AP3D1 is associated with five different SNPs located in the same gene. The SNPs in many olfactory transduction factor genes, OR51F1, OR8G1, and OR8G5, map to an eQTL in blood vessels for a common gene, VWA5A (von Willebrand factor A domain-containing protein 5A), which has been shown in a recent study to cause variations in the levels of circulating VWF protein and significantly impact survival after organ tx. Thus, functionally relevant variant differences between donor and recipient may not just relate to mismatched variants in specific genes between the pairs, but may also relate to other downstream genes that these variants may modify.

The application of VSURF, a strategy that uses the OOB error estimate and the variable importance measures from RF to build an algorithm that performs a variable selection method for each clinical endpoints (AMR, CMR, and NoRej), detected 65 variants, a subset of the 123 variants found with the Fisher's exact test, that classify all AMR, CMR, and NoRej samples perfectly in regards to patient outcomes after tx. Patients who developed CMR post-tx also had unique variants that relate primarily to gene function in CD4/CD8+ T cells, the prime cellular player in CMR. The NoRej group is well classified because these patients mostly lack any of the mismatches in the variants in the rejection groups.

In conclusion, herein is identified a finite and novel set of D/R specific mismatched variants that associate with high risk of rejection after tx and can discern between different histological and prognostic groups of either AMR or CMR after tx. This critical information can be obtained prior to tx surgery to select an optimal donor when more than one donor is being considered, or to assess post-tx rejection risk of AMR and CMR and personalize induction and maintenance immunosuppression to mitigate immune risk. Preventing rejection, specifically AMR, by optimizing donor selection, will have a significant positive on improving long-term tx outcomes.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of predicting transplant outcome for a selected graft type for a selected donor-recipient pair, comprising the steps of:
   obtaining a sample from the donor, and, by the sample, identifying the donor sequences expressed at one or more selected polymorphic loci of rejection-associated genetic mismatches;
   obtaining a sample from the recipient, and, by the sample, identifying the recipient sequences expressed at one or more selected polymorphic loci of rejection-associated genetic mismatches;
   wherein the sequences comprise a group of SNPs consisting of: rs1061040; rs12706498; rs12962744; rs20567; rs2066775; rs2072306; rs2074959; rs2243558; rs2251409; rs3803956; rs4807203; rs58394656; and rs8124907;
   compiling a mismatch profile comprising a set of mismatched sequences for the group of SNPs between the donor and recipient; and
   inputting the mismatch profile to a predictive model relating mismatches to transplant outcome, wherein the predictive model outputs a prediction of transplant outcome for the donor-recipient pair.

2. The method of claim 1, wherein the group of SNPs further comprises one or more additional SNPs selected from the group consisting of: rs1030723; rs1045631; rs1052748; rs10753428; rs10821071; rs10836609; rs10836610; rs10951; rs11033793; rs11079476; rs11102967; rs112380345; rs11405; rs11522329; rs11545028; rs12442401; rs1254677; rs1256522; rs1256523; rs12737742; rs12911191; rs13264965; rs170447; rs1796743; rs200242471; rs2043691; rs209727; rs2229868; rs2236910; rs2258835; rs2271804; rs2274716; rs2292000; rs2297499; rs2297674; rs2466613; rs2466636; rs2466701; rs2512167; rs2512168; rs2586306; rs2686409; rs2802267; rs284445; rs28620278; rs2961940; rs306456; rs3134421; rs34547900; rs3734518; rs3809805; rs3815625; rs3817699; rs3817700; rs4074317; rs4268525; rs4647954; rs4719110; rs4739138; rs4904448; rs4938316; rs4965642; rs55980973; rs574663; rs577219; rs635346; rs6439602; rs66932611; rs6992564; rs7029684; rs7071851; rs7107539; rs78118592; rs7839990; rs7858563; rs8096198; rs8101688; rs8565; rs871790; rs9933302; rs9940301; rs11247924; rs11247925; rs112586932; rs117918036; rs12191479; rs12293627; rs12562454; rs13074171; rs1573040; rs17046589; rs17696575; rs2231546; rs2231547; rs3745213; rs41282822; rs41282824; rs4719480; rs56307226; rs57268417; rs61884560; rs71255153; rs7448965; rs75004274; rs35674; rs720632; rs35670; and rs10502246.

3. The method of claim 2, wherein the one or more additional SNPs comprises at least one hundred SNPs selected from the group consisting of: rs1030723; rs1045631; rs1052748; rs10753428; rs10821071; rs10836609; rs10836610; rs10951; rs11033793; rs11079476; rs11102967; rs112380345; rs11405; rs11522329; rs11545028; rs12442401; rs1254677; rs1256522; rs1256523; rs12737742; rs12911191; rs13264965; rs170447; rs1796743; rs200242471; rs2043691; rs209727; rs2229868; rs2236910; rs2258835; rs2271804; rs2274716; rs2292000; rs2297499; rs2297674; rs2466613; rs2466636; rs2466701; rs2512167; rs2512168; rs2586306; rs2686409; rs2802267; rs284445; rs28620278; rs2961940; rs306456; rs3134421; rs34547900; rs3734518; rs3809805; rs3815625; rs3817699; rs3817700; rs4074317; rs4268525; rs4647954; rs4719110; rs4739138; rs4904448; rs4938316; rs4965642; rs55980973; rs574663; rs577219; rs635346; rs6439602; rs66932611; rs6992564; rs7029684; rs7071851; rs7107539; rs78118592; rs7839990; rs7858563; rs8096198; rs8101688; rs8565; rs871790; rs9933302; rs9940301; rs11247924; rs11247925; rs112586932; rs117918036; rs12191479; rs12293627; rs12562454; rs13074171; rs1573040; rs17046589; rs17696575; rs2231546; rs2231547; rs3745213; rs41282822; rs41282824; rs4719480; rs56307226; rs57268417; rs61884560; rs71255153; rs7448965; rs75004274; rs35674; rs720632; rs35670; and rs10502246.

4. The method of claim 2, wherein the transplant outcome includes AMR and the one or more additional SNPs comprises one or more AMR SNPs selected from the group consisting of: rs1030723; rs1045631; rs1052748; rs10753428; rs10821071; rs10836609; rs10836610; rs10951; rs11033793; rs11079476; rs11102967; rs112380345; rs11405; rs11522329; rs11545028; rs12442401; rs1254677; rs1256522; rs1256523; rs12737742; rs12911191; rs13264965; rs170447; rs1796743; rs200242471; rs2043691; rs209727; rs2229868; rs2236910; rs2258835; rs2271804; rs2274716; rs2292000; rs2297499; rs2297674; rs2466613; rs2466636; rs2466701; rs2512167; rs2512168; rs2586306; rs2686409; rs2802267; rs284445; rs28620278; rs2961940; rs306456; rs3134421; rs34547900; rs3734518; rs3809805; rs3815625; rs3817699; rs3817700; rs4074317; rs4268525; rs4647954; rs4719110; rs4739138; rs4904448; rs4938316; rs4965642; rs55980973; rs574663; rs577219; rs635346; rs6439602; rs66932611; rs6992564; rs7029684; rs7071851; rs7107539; rs78118592; rs7839990; rs7858563; rs8096198; rs8101688; rs8565; rs871790; rs9933302; and rs9940301.

5. The method of claim 2, wherein the transplant outcome includes CMR and the one or more additional SNPs comprises one or more CMR SNPs selected from the group consisting of: rs11247924; rs11247925; rs112586932; rs117918036; rs12191479; rs12293627; rs12562454;

rs13074171; rs1573040; rs17046589; rs17696575; rs2231546; rs2231547; rs3745213; rs41282822; rs41282824; rs4719480; rs56307226; rs57268417; rs61884560; rs71255153; rs7448965; and rs75004274.

6. The method of claim 1, wherein the transplant outcome includes AMR and no rejection and wherein an AMR outcome is predicted by the occurrence of a greater number of mismatches.

7. The method of claim 1, wherein the donor-recipient pair is a prospective donor-recipient pair.

8. The method of claim 1, wherein the donor-recipient pair is a realized donor-recipient pair wherein the recipient has received a graft from the donor.

9. The method of claim 1, wherein the selected graft comprises a graft selected from the group consisting of kidney, heart, lung, liver, skin, cornea, intestine, pancreas, limb, digit, bone, ligament, cartilage, and tendon.

10. The method of claim 9, wherein the graft is a kidney graft.

11. The method of claim 1, wherein the sample comprises a biological material selected from the group consisting of blood, serum, tissue, graft tissue, interstitial fluid, skin, and an oral swab.

12. The method of claim 1, wherein the output of the predictive model is an index score, a probability score, or a classification.

* * * * *